US006007845A

United States Patent [19]
Domb et al.

[11] Patent Number: 6,007,845
[45] Date of Patent: *Dec. 28, 1999

[54] NANOPARTICLES AND MICROPARTICLES OF NON-LINEAR HYDROPHILIC-HYDROPHOBIC MULTIBLOCK COPOLYMERS

[75] Inventors: Abraham J. Domb, Efrat, Israel; Ruxandra Gref, Nancy, France; Yoshiharu Minamitake, Gumma, Japan; Maria Teresa Peracchia, Parma, Italy; Robert S. Langer, Newton, Mass.

[73] Assignee: Massachusetts Institute of Technology, Cambridge, Mass.

[*] Notice: This patent is subject to a terminal disclaimer.

[21] Appl. No.: 08/582,993
[22] PCT Filed: Jul. 22, 1994
[86] PCT No.: PCT/US94/08287
  § 371 Date: Jan. 22, 1996
  § 102(e) Date: Jan. 22, 1996
[87] PCT Pub. No.: WO95/03356
  PCT Pub. Date: Feb. 2, 1995

[51] Int. Cl.$^6$ .............................. A61K 9/50; A61K 9/14; A61K 9/16; A61K 9/48
[52] U.S. Cl. ......................... 424/501; 424/489; 424/497; 424/498; 424/502; 424/451; 424/462; 424/78.08; 514/772.3; 514/784; 514/963; 514/402.21; 428/402.24
[58] Field of Search ................................ 424/78.08, 462, 424/451, 502, 498, 489, 497, 1–11, 9.4, 9.411, 9.5, 452; 514/772.3, 784, 963, 402.21; 428/402.21, 402.24, 403

[56] References Cited

U.S. PATENT DOCUMENTS

| | | |
|---|---|---|
| 4,501,726 | 2/1985 | Schröder et al. . |
| 4,757,128 | 7/1988 | Domb et al. . |
| 4,789,724 | 12/1988 | Domb et al. . |
| 4,801,739 | 1/1989 | Franz et al. . |
| 4,857,311 | 8/1989 | Domb et al. . |
| 4,888,176 | 12/1989 | Langer et al. ........................... 424/426 |
| 4,904,479 | 2/1990 | Illum ........................................ 424/490 |
| 5,133,908 | 7/1992 | Stainmesse et al. . |
| 5,141,739 | 8/1992 | Jung et al. .................................. 424/4 |
| 5,145,684 | 9/1992 | Liversidge et al. . |
| 5,149,543 | 9/1992 | Cohen et al. . |
| 5,410,016 | 4/1995 | Hubbell et al. .......................... 528/354 |
| 5,565,215 | 10/1996 | Gref et al. ............................... 424/501 |
| 5,578,325 | 11/1996 | Domb et al. ............................. 424/501 |

FOREIGN PATENT DOCUMENTS

| | | |
|---|---|---|
| 0 092 918 | 11/1983 | European Pat. Off. . |
| 0 166 596 | 1/1986 | European Pat. Off. . |
| 0 295 055 | 12/1988 | European Pat. Off. . |
| 0 520 888 A1 | 6/1992 | European Pat. Off. . |
| 0 520 889 A1 | 6/1992 | European Pat. Off. . |
| 0 552 802 | 7/1993 | European Pat. Off. . |
| WO 94/02122 | 2/1994 | WIPO . |

OTHER PUBLICATIONS

Agostini, S., "Synthesis and Characterization of PHB," Ph.D. thesis Case Western University, U.S.A. (1971).

Allen, T.M. and Hansen, C., "Pharmacokinetics of stealth versus conventional liposomes: effect of dose," Biochimica et *Biophysica Acta*, 1068: 133–141 (1991).

Allen, T.M., et al., "Liposomes containing synthetic lipid derivatives of poly(ethylene glycol) show prolonged circulation half–lives in vivo," *Biochimica et Biophysica Acta*, 1066: 29–36 (1991).

Deng, X.M., et al., *J. of Polymer Science: Part C: Polymer Letters*, 28: 411–416 (1990).

Illum., L. and Davis, S.S., "The organ uptake of intravenously administered colloidal particles can be altered by using a non–ionic surfactant (Poloxamer 338)," *FEBS Lett.* 1212, 167(1): 79–82 (1984).

Klibanov, A., et al., "Activity of amphipathic poly(ethylene glycol) 5000 to prolong the circulation time of liposomes depends on the liposome size and is unfavorable for immunoliposome binding to target," *Biochimica et Biophysics Acta*, 1062: 142–148 (1991).

Lasic, D.D., et al., "Sterically stabilized liposomes: a hypothesis on the molecular origin of the extended circulation times," *Biochimica et Biophysica Acta*, 1070: 187–192 (1991).

Maruyama, K., et al., "Effect of Molecular Weight in Amphipathyic Polyethyleneglycol on Prolonging the Circulation Time of Large Unilamellar Liposomes," *Chem. Pharm. Bull.*, 39(6): 1620–1622 (1991).

(List continued on next page.)

*Primary Examiner*—Lynette R. F. Smith
*Assistant Examiner*—Datquan Lee
*Attorney, Agent, or Firm*—Arnall Golden & Gregory, LLP

[57] ABSTRACT

Particles are provided that are not rapidly cleared from the blood stream by the macrophages of the reticuloendothelial system, and that can be modified to achieve variable release rates or to target specific cells or organs. The particles have a core of a multiblock copolymer formed by covalently linking a multifunctional compound with one or more hydrophobic polymers and one or more hydrophilic polymers, and contain a biologically active material. The terminal hydroxyl group of the poly(alkylene glycol) can be used to covalently attach onto the surface of the particles biologically active molecules, including antibodies targeted to specific cells or organs, or molecules affecting the charge, lipophilicity or hydrophilicity of the particle. The surface of the particle can also be modified by attaching biodegradable polymers of the same structure as those forming the core of the particles. The typical size of the particles is between 180 nm and 10,000 nm, preferably between 180 nm and 240 nm, although microparticles can also be formed as described herein. The particles can include magnetic particles or radiopaque materials for diagnostic imaging, biologically active molecules to be delivered to a site, or compounds for targeting the particles. The particles have a prolonged half-life in the blood compared to particles not containing poly(alkylene glycol) moieties on the surface.

38 Claims, 7 Drawing Sheets

OTHER PUBLICATIONS

Torchilin, V. and Klibanov, A., "The Antibody–Linked Chelating Polymers for Nuclear Therapy And Diagnostics", *Critical Reviews in Therapeutic Drug Carrier Systems*, 7(4): 275–308 (1991).

Woodle, M.C., et al., "Versatility in lipid compositions showing prolonged circulation with sterically stabilized liposomes," *Biochimica et Biophysica Acta*, 1105: 193–200 (1992).

Zhu, K.J., et al., "Preparation Characterization and Properties of Polylactide (PLA)–Poly(ethylene Glycol) (PEG) Copolymers: A Potential Drug Carrier," *J. App. Polym. Sci.*, 39: 1–9 (1990).

Brich, Z., et al., "Branched Ter–Polyesters: Synthesis, Characterization, In Vitro and In Vivo Degradation Behaviour", *Proceed. Intern. Symp. Control. Rel. Bioact. Mater.* 15:95–96 (1988).

Jedlinsk, Zbigniew, et al., "Synthesis of ethylene glycol–L–lactide block copolymers," Makromol. Chem. 194:1681–1689 (1993).

OTHER STRUCTURES

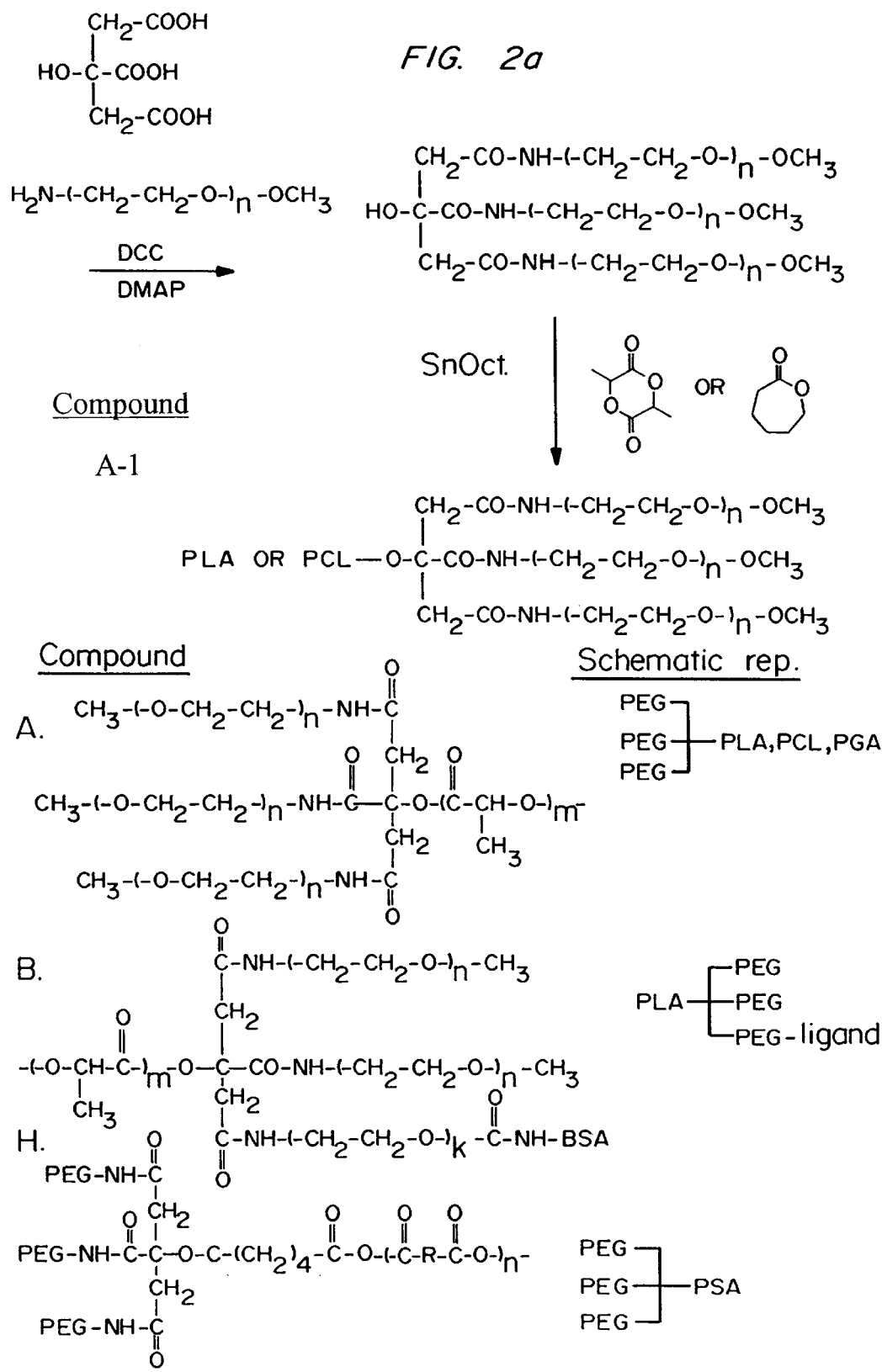

G.

I.

OR

I-1.

J.

L.

M.

NANOPARTICLES AND MICROPARTICLES OF NON-LINEAR HYDROPHILIC-HYDROPHOBIC MULTIBLOCK COPOLYMERS

The United States Government has certain rights in this invention by virtue of Grant Number NIH-1R01-GM44884 awarded by the National Institutes of Health.

This invention is in the area of biodegradable block copolymers and nanoparticles and microparticles for the controlled delivery of biologically active material and diagnostic purposes made from the polymers.

BACKGROUND OF THE INVENTION

A major challenge in the area of the parenteral administration of biologically active materials is the development of a controlled delivery device that is small enough for intravenous application and which has a long circulating half-life. Biologically active materials administered in such a controlled fashion into tissue or blood are expected to exhibit decreased toxic side effects compared to when the materials are injected in the form of a solution, and may reduce degradation of sensitive compounds in the plasma.

A number of injectable drug delivery systems have been investigated, including microcapsules, microparticles, liposomes and emulsions. A significant obstacle to the use of these injectable drug delivery materials is the rapid clearance of the materials from the blood stream by the macrophages of the reticuloendothelial system (RES). For example, polystyrene particles as small as sixty nanometers in diameter are cleared from the blood within two to three minutes. By coating these particles with block copolymers based on poly(ethylene glycol) and poly(propylene glycol), their half-lives were significantly increased. L. Illum, S. S. Davis, "The organ uptake of intravenously administered colloidal particles can be altered by using a non-ionic surfactant (poloxamer 338)", *FEBS Lett.*, 167, 79 (1984).

Liposomal drug delivery systems have been extensively considered for the intravenous administration of biologically active materials, because they were expected to freely circulate in the blood. It was found, however, that liposomes are quickly cleared from the blood by uptake through the reticuloendothelial system. The coating of liposomes with poly(ethylene glycol) increases their half life substantially. The flexible and relatively hydrophilic PEG chains apparently induce a stearic effect at the surface of the liposome that reduces protein adsorption and thus RES uptake. T. M. Allen, C. Hansen, *Biochimica et Biophysica Acta,* 1068, 133–141 (1991); T. M. Allen, et al., *Biochimica et Biophysica Acta,* 1066, 29–36 (1991); V. Torchilin, A. Klibanov, "The Antibody-linked Chelating Polymers for Nuclear Therapy and Diagnostics", *Critical Reviews in Therapeutic Drug Carrier Systems,* 7(4), 275–307 (1991); K. Maruyama, et al., *Chem. Pharm. Bull.,* 39(6), 1620–1622 (1991); M. C. Woodle, et al., *Biochimica et Biophysica Acta;* 193–200 (1992); and D. D. Lassic, et al., *Biochimica et Biophysica Acta,* 1070, 187–192 (1991); and A. Klibanov, et al., *Biochimica et Biophysica Acta,* 1062, 142–148 (1991).

European Patent Application Nos. 0 520 888 A1 and 0 520 889 A1 disclose nanoparticles made from linear block copolymer of polylactic acid and poly(ethylene glycol) for the controlled administration of biologically active materials. The applications do not disclose how to modify the copolymer to vary the profile of drug release or how modifying the copolymer would affect distribution and clearance of the delivery devices in vivo. The applications also do not teach how to prepare nanoparticles that are targeted to specific cells or organs, or how to prepare nanospheres that are useful for gamma-imaging for diagnostic purposes.

In U.S. Ser. No. 08/690,370 filed Jul. 23, 1993, injectable particles are described which are formed of a biodegradable solid core containing a biologically active material and poly(alkylene glycol) moieties on the surface or of block copolymers of the poly(alkylene glycol) moieties with biodegradable polymers, which exhibit increased resistance to uptake by the reticuloendothelial system.

It would be desirable to have other types of particles for the controlled delivery of materials that are not rapidly cleared from the blood stream by the macrophages of the reticuloendothelial system, and that can be modified as necessary to target specific cells or organs or manipulate the rate of delivery of the material.

It is an object of the present invention to provide copolymers for preparing microparticles or nanoparticles or coatings which decrease uptake by the reticuloendothelial system and are readily derivatized.

It is another object of the present invention to provide particles for the controlled delivery of diagnostic and therapeutic materials that are not rapidly cleared from the blood stream.

It is another object of the present invention to provide microparticles or nanoparticles that can be modified as necessary to target specific cells or organs or manipulate the rate of delivery of the material.

It is another object of the present invention to provide biodegradable microparticles or nanoparticles that contain detectable materials for diagnostic imaging.

SUMMARY OF THE INVENTION

Non-linear multiblock copolymers are prepared by covalently linking a multifunctional compound with one or more hydrophilic polymers and one or more hydrophobic bioerodible polymers to form a polymer including at least three polymeric blocks. In one embodiment, one or more hydrophilic polymers, such as polyethylene glycol (PEG) chains or polysaccharide moieties, are covalently attached to a multifunctional molecule such as citric acid or tartaric acid, leaving one or more active hydroxyl, carboxylic acid or other reactive functional groups available to attach the hydrophobic polymer(s). The hydrophobic polymer, such as polylactic acid (PLA), polyglycolic acid (PGA), polyanhydrides, polyphosphazenes or polycaprolactone (PCL), is then covalently linked to the multifunctional compound via an appropriate reaction such as ring opening or condensation polymerization. In one embodiment, the multiblock copolymers can have several short PEG chains, for example, with a molecular weight less than 1000, attached to the multifunctional compound. Ligands can be attached to one or more polymer chains to achieve a variety of properties for a wide range of applications.

The block copolymers are useful in forming coatings on implantable devices and, in the most preferred embodiment, nanoparticles and microparticles that are not rapidly cleared from the blood stream by the macrophages of the reticuloendothelial system, and that can be modified as necessary to achieve variable release rates or to target specific cells or organs as desired. The particles can incorporate within or on their surface a substance to be delivered for either therapeutic or diagnostic purposes. In a preferred embodiment, the hydrophilic polymer is a poly(alkylene glycol) (PAG). The terminal hydroxyl group of the poly(alkylene glycol) or other hydrophilic polymers can be used to covalently attach molecules onto the surface of the particles. Materials incorporated onto or within the particles include biologically active molecules and targeting molecules such as antibodies immunoreactive with specific cells or organs, compounds specifically reactive with a cell surface component, magnetic particles, detectable materials such as radiopaque materials for diagnostic imaging, other substances detectable by x-ray or ultrasound such as air, fluorescence, magnetic resonance imaging, and molecules affecting the charge, lipophilicity or hydrophilicity of the particle.

The typical size of the particles is between approximately 80 nm and 10,000 nm, preferably between 80 nm and 400 nm, although microparticles can also be formed as described herein. The particles can be administered by a variety of ways, although a preferred embodiment is by intravenous administration. The particles are easily lyophilized and redispersed in aqueous solutions. Biodistribution experiments indicate that the particles have a prolonged half-life in the blood compared to particles not containing poly(alkylene glycol) moieties on the surface.

BRIEF DESCRIPTION OF THE FIGURES

FIG. 2a is a schematic illustration of the synthesis of (PEG)$_3$-citrate-polylactide, (PEG)$_3$-citrate-polycaprolactone and (PEG)$_3$-citrate-polysebacic acid, in which the polyethylene glycol blocks can be functionalized with a ligand.

Figure 1A:
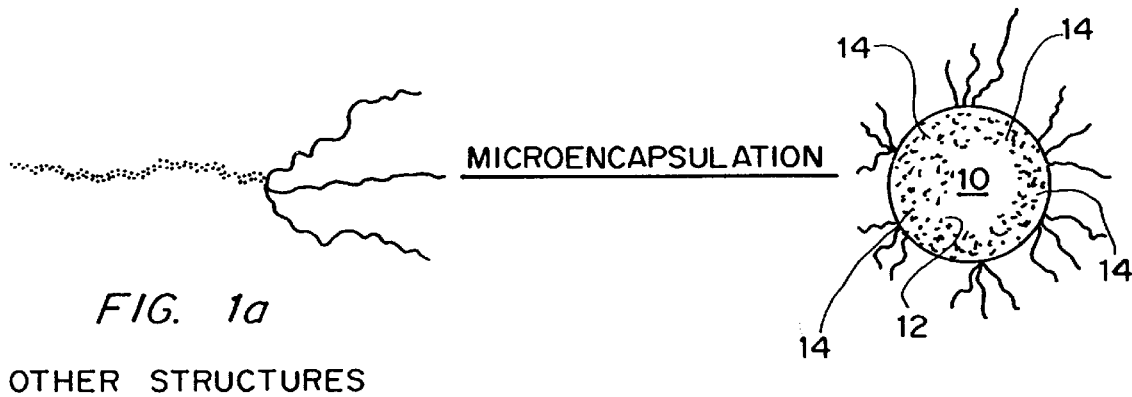
FIGS. 1a, 1b, and 1c are schematic representations of nanospheres formed of multiblock copolymers made by covalently linking a multifunctional compound with one or more hydrophilic polymers and one or more hydrophobic bioerodible polymers.

The non-linear block copolymers in each of FIGS. 2a through 2i were synthesized from poly(ethylene glycol) [PEG] of the molecular weights 600, 1900, 5,000; 12,000; and 20,000, and polylactide (PLA), polyglycolide, polycaprolactone (PCL), or polysebacic anhydride (PSA).

DETAILED DESCRIPTION OF THE INVENTION

Non-linear multiblock copolymers are prepared by covalently linking a multifunctional compound with one or more hydrophilic polymers and one or more hydrophobic bioerodible polymers to form a polymer including at least three polymeric blocks. In one embodiment, one or more hydrophilic polymers, such as polyethylene glycol (PEG) chains or polysaccharide moieties, are covalently attached to a multifunctional molecule such as citric acid or tartaric acid, leaving one or more active hydroxyl, carboxylic acid or other reactive functional groups available to attach the hydrophobic polymer(s). The hydrophobic polymer, such as polylactic acid (PLA), polyglycolic acid (PGA), polyanhydrides, polyphosphazenes or polycaprolactone (PCL), is then covalently linked to the multifunctional compound via an appropriate reaction such as ring opening or condensation polymerization.

Particles formed of the coblock polymers are disclosed that are not rapidly cleared from the blood stream by the macrophages of the reticuloendothelial system as the particles not surface modified with hydrophilic polymers, and that can be modified as necessary to achieve variable release rates or to target specific cells or organs as desired. The particles are useful to administer biologically active materials in a controlled manner for a wide variety of purposes.

I. Non-linear Block Copolymers

Selection of Polymers

Hydrophilic Polymers

Hydrophilic polymers, including but not limited to poly (alkylene glycols) (which can also be referred to as a poly(alkylene oxide), if the polymer was prepared from an oxide instead of a glycol) and polysaccharides, are employed as the hydrophilic portion of the multiblock copolymer. Hydrophilic polymers other than poly(alkylene glycol) that can be used include polypyrrolidone, poly (amino acids), including short non-toxic and non-immunogenic proteins and peptides such as human albumin, fibrin, gelatin and fragments thereof, dextrans, and poly (vinyl alcohol). Other materials include a Pluronic™ F68 (BASF Corporation), a copolymer of polyoxyethylene and polyoxypropylene, which is approved by the U.S. Food and Drug Administration (FDA).

As used herein, the term poly(alkylene glycol) refers to a polymer of the formula HO-[(alkyl)O]$_y$-OH, wherein alkyl refers to a C$_1$ to C$_4$ straight or branched chain alkyl moiety, including but not limited to methyl, ethyl, propyl, isopropyl, butyl, and isobutyl. Y is an integer greater than 4, and typically between 8 and 500, and more preferably between 40 and 500.

In vivo results show that the higher the molecular weight (MW) of PEG, the longer the circulation time in the blood (the half-life).

Specific examples of poly(alkylene glycols) include poly (ethylene glycol), polypropylene 1,2-glycol, poly(propylene oxide) and polypropylene 1,3-glycol. A preferred hydrophilic polymeric moiety is PEG of a molecular weight of between approximately 300 to 20,000.

To ensure elimination from the body, the molecular weight of the polyethylene glycol should be between approximately 300 and 20,000 Daltons, the molecular weight of polysaccharides should be 40,000 or less, and the molecular weight of proteins should be 70,000 or less.

Hydrophobic Polymers

The hydrophobic polymer should be bioerodible, biocompatible, and have a terminal group that can react with the terminal functional group, such as a hydroxyl, thiol, amino, carboxy, aldehyde or other functional group of the multifunctional molecule to form a covalent linkage. Multiblock copolymers containing polylactic acid moieties are a preferred embodiment. However, the copolymer of lactic acid and glycolic acid, as well as other polymers such as polyanhydrides, polyphosphazenes, polymers of α-hydroxy carboxylic acids, polyhydroxybutyric acid, polyorthoesters, polycaprolactone, polyphosphates, or copolymers prepared from the monomers of these polymers can be used to form the multiblock copolymers described herein. The variety of materials that can be used to prepare the block copolymers forming the particles significantly increases the diversity of release rate and profile of release that can be accomplished in vivo.

In a preferred embodiment, a polyester of poly(lactic-co-glycolic)acid (PLGA) is used as a hydrophobic erodible polymer bound to the multifunctional compound. These polymers are approved for parenteral administration by the FDA. Because PLGA degrades via hydrolysis, in vivo degradation rates can be predicted from in vitro data. PLGA degrades to lactic and glycolic acids, substances found naturally in the body. Furthermore, by manipulating the molar ratio of lactic and glycolic acid and the molecular weight of the copolymers, different degradation patterns can be obtained.

The molecular weight and the chemical composition and stereochemical configuration of the polymer will affect the solubility of the polymer in various organic solvents as well as the crystallinity of the polymer. In this regard, a copolymer of lactic acid and glycolic acid is preferable.

Preferably, the hydrophobic, bioerodible polymers are soluble in ethyl acetate or acetone. Ethyl acetate or acetone is preferred over other organic solvents such as dichloromethane and chloroform because they are less toxic for in vivo applications.

Poly L-lactide is a polymer with a high degree of crystallinity. Poly D,L-lactide is less crystalline and more soluble in organic solvents. A random copolymer of D,L-lactide and glycolide in the ratio of 75:25 is very soluble in organic solvents, in particular in ethyl acetate. This copolymer is completely amorphous, which renders it a useful polymer for the fabrication of nanospheres and microspheres for controlled release.

Poly-L-lactide has a degradation time in vitro of months to years. The long degradation time is due to its higher crystallinity which protects the polymer from water penetration. Since D,L-lactide is amorphous, its degradation time is typically one to a number of months. Poly-glycolide also has a crystalline structure and a degradation time of one to several months. D,L-PLGA is amorphous, with a degradation time in vitro of weeks to months. As the glycolic acid ratio is increased, the rate of degradation is enhanced. Lactic acid has bulky methyl groups on the alpha carbon (—O—CH(CH$_3$)—CH—) which makes it difficult for water molecules to access the ester, while glycolic acid has a proton on the alpha carbon (—O—CH$_2$—CO—), which allows easier access of water molecules to the ester bonds.

The molecular weight of the hydrophilic and hydrophobic regions of the particle affect the water solubility of the particles and thus their stability in aqueous solutions.

Preparation of Multiblock Copolymers

The multiblock copolymers formed by covalently linking a multifunctional compound with one or more hydrophilic polymers, preferably poly(alkylene glycol) (PAG), more preferably poly(ethylene glycol), and one or more hydrophobic polymers can be prepared by a number of methods. One method involves protecting one end of the hydrophilic polymer, for example, polyethylene glycol, and reacting the functional group at the unprotected end with one or more reactive groups on the multifunctional compound. Then, the remaining reactive groups on the multifunctional compound can be reacted with one or more hydrophobic bioerodible polymers, followed by removal of the protecting groups. Selective removal of the protecting groups allows selective modification of the hydrophobic and hydrophilic polymers, and is well known to those skilled in the art of polymer synthesis.

Preferred protected polyalkylene glycols include monomethoxy poly(alkylene glycols), such as monomethoxy-PEG or PEG protected with another oxygen protecting group known to those of skill in the art, such that one terminal hydroxyl group is protected and the other is free to react with the polymer.

A second method involves reacting a hydrophobic bioerodible polymer, with one terminal functional group protected, with one or more reactive groups on the multifunctional compound, and then reacting a protected hydrophilic polymer with one or more reactive groups remaining on the multifunctional compound.

In an alternative embodiment, a carboxylic acid group on the multifunctional compound can be reacted with a poly(alkylene glycol) terminated with an amino function (available from Shearwater Polymers, Inc.) to form an amide linkage, which is in general stronger than an ester linkage. The amide linkage may provide a longer period of retention of the poly(alkylene glycol) on the surface of the nanoparticle. Methods of linking amino groups with carboxylic acid groups to form amides are well known to those skilled in the art.

In another alternative embodiment, a thiol group on a polymer can be reacted with a carboxy group on the multifunctional compound to form a thioester linkage. Methods of forming thioester linkages are known to those skilled in the art.

In yet another alternative embodiment, amino groups on a polymer can be coupled with amino groups on a multifunctional compound using a crosslinking agent such as glutaraldehyde. These coupling reactions are known to those skilled in the art.

Other multiblock copolymers terminated with poly(alkylene glycol), and in particular, poly(ethylene glycol), can be prepared using the reactions described above, using a branched or other suitable poly(alkylene glycol) and protecting the terminal groups that are not to be reacted. Shearwater Polymers, Inc., provides a wide variety of poly(alkylene glycol) derivatives.

In one embodiment, a multiblock copolymer is prepared by reacting the terminal group of the hydrophobic polymeric moiety such as PLA or PLGA with a suitable polycarboxylic acid monomer, including but not limited to 1,3,5-benzenetricarboxylic acid, butane-1,1,4-tricarboxylic acid, tricarballylic acid (propane-1,2,3-tricarboxylic acid), and butane-1,2,3,4-tetracarboxylic acid, wherein the carboxylic acid moieties not intended for reaction are protected by means known to those skilled in the art. The protecting groups are then removed, and the remaining carboxylic acid groups reacted with a hydrophilic polymer, such as a poly(alkylene glycol). In another alternative embodiment, a di, tri, or polyamine is similarly used as the branching agent.

II. Preparation of Particles from Block Copolymers

Preparation and Characterization of Nanoparticles

Nanospheres can be prepared from the block copolymers by emulsion/evaporation techniques using the pre-formed copolymer. The pre-formed polymer and, optionally, a substance to be delivered, if soluble in an organic solvent, can be dissolved in an organic solvent. Loadings can be about 25 mg polymer/2 ml methylene chloride, and the substance to be delivered in approximately between 10% and 50% of the weight of the polymer. The resulting organic solution can be emulsified with an aqueous phase by vortexing and then sonicated, typically for 1 minute, at approximately a 40 watt output. The solvent can be evaporated and the nanospheres can be collected by centrifugation (30 min, 5,000 rpm), washed twice and lyophilized.

Amphiphilic multiblock copolymers can form nanospheres with a biodegradable and dense core able to entrap drugs or other compounds, and with an effective coating to prevent the rapid recognition by the immune system. The different solubilities of the hydrophilic and hydrophobic blocks, for example, PEG and a polyester or polyanhydride, in water and organic solvents allows one to obtain the desired phase-separated structure of the nanospheres. The organic phase, containing polymer and drug, can be emulsified with water without adding any further stabilizer, because of the surfactant properties of the multiblock copolymer. By emulsifying the two phases, the hydrophilic block migrates to the water interface, and the hydrophobic block remains inside the droplets and forms the solid biodegradable core after solvent evaporation. Sub-200 nm size particles with a high PEG density on the surface can be obtained using a high energy form such as ultrasound. AFM analysis indicates that nanospheres prepared in this manner are spherical, and QELS showed that the particle size of nanospheres prepared in this manner are in the range of between 180 and 240 nm and have a unimodal size distribution.

For example, the mixture of block copolymer and substance to be delivered can be mixed in a common solvent such as ethyl acetate or methylene chloride. Preferably, the organic solvent is a nonsolvent for the hydrophilic polymers, and a solvent for the hydrophobic polymers. An emulsion can be formed by adding water, preferably distilled deionized water, to the solution. Slow evaporation of the organic solvent allows a reorganization of the polymer chains inside and on the surface of the droplets. The hydrophilic polymers, which are preferably insoluble in the organic solvent, tend to migrate to the aqueous phase, while the hydrophobic polymers, which are not soluble in water, remain inside the droplets and forms the core of the nanospheres after the solvent is evaporated. PEG chains inside the core should be avoided, because this can lead to absorption of water by the core followed by the accelerated and uncontrolled release of the drugs.

After removing the organic solvent, the particles can be isolated from the aqueous phase by centrifugation. They can later be readily redispersed in water.

In an alternative embodiment, acetone, methanol, or ethanol and their aqueous solutions can be used in place of the distilled deionized water. In general, water is preferred because it forces a higher concentration of poly(alkylene glycol) to the surface of the particle. However, acetone can be used as the precipitating solvent if the hydrophobic polymer, for example, polyanhydride, is sensitive to water.

In another alternative embodiment, the multiblock copolymer can be blended with a linear hydrophobic-hydrophilic copolymer, for example PLGA-PEG mixed with PLGA or PLA, prior to fabrication into the particles, to provide different properties on the particles, for example, altering their half-life in vivo. Adding PLGA-PEG to other polymers can increase the in vivo half-life of the particles.

In a typical embodiment, the linear copolymer can be mixed with the multiblock copolymer in a ratio of greater than 0 up to 100 percent by weight and optimally, between 10 and 100 percent by weight.

The substance to be delivered can be mixed with the copolymer or copolymer blend in a ratio of greater than 0 to 99, and more preferably, in a ratio of 1 to 70.

Characterization studies were carried out at different drug loadings to investigate encapsulation properties and morphological characteristics of PEG-polyanhydride and PEG-polyester nanospheres. Particle size was measured by quasi-elastic light scattering (QELS). The instruments used were a Lexel Argon-ion laser (Fremont, Calif., USA) (model BI-200SM), with a Brookhaven apparatus consisting of a goniometer and a 136 channel digit correlator and a signal processor. Measurements were made with a laser at a wavelength of 488 nm at a scattering angle of 90°. The image of the nanospheres was taken by atomic force microscopy (AFM). The apparatus (Nanoscope III, Digital Instruments, Santa Barbara, Calif., USA) consisted of a cantilever oscillating vertically (tapping mode) with a frequency of 350 kHz.

Chemical surface analysis (XPS) was performed to check for the presence of PEG on the nanospheres surface, and to investigate the presence of drug molecules located on the surface. Data were collected by MgKα x-rays with a power of 300 W on a Perkin-Elmer 5100 apparatus.

To check polymer degradation, lactic acid was detected by colorimetric method using Lactate Reagent (Sigma) for a quantitative determination of lactate at 540 nm.

Differential scanning calorimetry (DSC) was performed to detect drug crystallization inside the nanospheres and to investigate any possible interaction between the drug and the polymer.

Morphological analysis of the nanosphere inner core was carried out by transmission electron microscopy of a cross-section of samples obtained by freeze fracture.

Drug loading was measured by dissolving lyophilized nanospheres into an appropriate solvent and assaying the amount of drug (lidocaine or prednisolone) spectrophotometrically.

PEG-coated nanospheres are examples of preferred nanospheres, and can be prepared from multiblock copolymers formed by covalently linking a multifunctional compound with at least one poly(ethylene glycol) (PEG) and at least one hydrophobic bioerodible polymer, such as a polyester, for example, (poly(D,L lactic acid), or poly(lactic co-glycolic acid), a polylactone such as ε-polycaprolactone) or a polyanhydride, such as (poly(sebacic acid).

Light scattering studies have indicated that the size of the resulting particles can be determined by the viscosity of the organic phase, ratio of organic to aqueous phase, and sonication power and time. Increased viscosity yields bigger particles and a higher ratio of the aqueous phase volume as compared to organic phases yields smaller particles. An example of the effect of the sonication power and time is as follows: 25 mg polymer/2 ml $CH_2Cl_2$ is added to 30 ml of 0.3% polyvinyl alcohol solution. The mixture is vortexed for 30 seconds at the maximum strength and then sonicated by probe sonicator for 30 seconds at the output 7. The conditions can reproducibly yield nanoparticles of a particle size of between 180 and 240 nm. These parameters can be optimized to obtain nanospheres having desired size range with a narrow unimodal size distribution of about 200 nm.

Using non-linear block copolymers, the density of the hydrophilic block at the nanosphere surface can be increased and blood circulation of these carriers can be prolonged, relative to using a linear copolymer. When multiblock copolymers containing multiple PEG blocks are used, there is typically more PEG on the surface of nanospheres prepared from brush copolymers than on the surface of nanospheres prepared from linear copolymers, as shown by ESCA. The amount of PEG (deducted from the ratio between PEG and PLA or PLGA comparing C peaks convolution) can be increased from 35.65% to more than 44% using non-linear multiblock copolymers as compared with linear copolymers.

Other characterization studies were carried out to investigate morphological characteristics and encapsulation properties of PEG-polyanhydride and PEG-polyester nanospheres, at different drug loadings. Cross-section images of freeze-fractured nanospheres were obtained by TEM, showing the particle dense core. Partial drug recrystallization was shown by DSC data.

The chemical composition of the nanosphere can be important to the determination of the final particle size. Nanospheres prepared from multiblock brush copolymers that include a significant amount of PEG on the surface of the particle are typically in the size range of 180 nm or greater. The diameter can increase up to 240 nm in the case of the highest PEG m.w. in (PEG 20K)$_3$-PLA particles, in contrast to PLA nanoparticles, where the diameter can be less than 120 nm. Surprisingly, this is in contrast to particles prepared from linear copolymers, such as PEG-PLGA particles, in which the PEG in PEG-PLGA particles was able to reduce nanosphere size, as compared to not-coated particles. The composition of the hydrophobic block(s) also affects the particle size. For example, using polycaprolactone, which is more soluble in methylene chloride, to form the nanosphere core, particles with a diameter of less than 100 nm can be obtained. Drug loading appears to have little effect on particle size. Particles loaded with lidocaine and prednisolone can show the same size even when the amount of drug loaded is as high as 45%.

Preparation of Microparticles

Microparticles can be prepared using the methods as described above for preparing nanoparticles, without using an ultrasonic bath. The microparticles can also be prepared by spraying a solution of the multiblock copolymer in organic solvent into an aqueous solution.

Composition of Particles

As described above, particles are formed from multiblock copolymers prepared by covalently linking a multifunctional compound with at least one hydrophilic polymer, such as a poly(alkylene glycol) with a molecular weight of between 300 and 20,000 or a polysaccharide moiety, and at least one hydrophobic polymer, such as polyorthoesters, polyphosphate esters, poly(lactic-co-glycolic acid), poly(lactic acid), poly(glycolic acid), polyanhydride, polyphosphazenes, polycaprolactone or other biodegradable, biocompatible polymers, and copolymers thereof. The multifunctional compound can be substituted with between one and ten hydrophilic polymers and between one and ten hydrophobic polymers, and preferably is substituted with between one and six hydrophilic polymers and between one and six hydrophobic polymers.

As used herein, a hydrophilic polymer refers to a polymer that is soluble in aqueous medium, and if used for medical applications, is biocompatible and readily eliminated from the human body. The preferred molecular weight for PEG is between 300 and 20,000, for polysaccharides, between 1,000 and 40,000, and for polyamino acids (peptides), between 1,000 and 70,000.

As used herein, a hydrophobic bioerodible polymer refers to a polymer that is insoluble in aqueous medium, but may absorb water up to 30% of its weight, and is biocompatible and degradable. Preferred molecular weight ranges are between 500 and 500,000.

As used herein, a polysaccharide refers to a carbohydrate composed of many monosaccharides.

As used herein, a multifunctional compound refers to a compound with at least two functional groups capable of being coupled with functional groups on a polymer. The compound can be a linear, branched or cyclic alkyl group, an aromatic group, a heterocyclic group, or a combination thereof. The types of groups include, but are not limited to, hydroxyl, thiol, amino, carboxylic acid, aldehyde, sulfonic acid, phosphoric acid, amide, isocyanate, imine and derivatives thereof. Preferably, the compound is non-toxic and biodegradable. Examples of preferred multifunctional compounds include, but are not limited to, tartaric acid, mucic acid, citric acid, glucaronic acid and tri, tetra- and polycarboxylic acids, including benzene tetracarboxylic acid, dextrins and tri, tetra and polyalcohols, and molecules with combinations of carboxyl and hydroxyl groups.

Size of Particles

As described herein, the typical size of the particles is between 80 nm and 10,000 nm, preferably between 80 nm and 400 nm. The methodology produces particles between 80 and 10,000 nm, i.e., both nanoparticles, and microparticles having a diameter of 1 micron or greater. For ease of reference herein in the general descriptions, both microparticles and nanoparticles will be referred to as particles unless otherwise specified.

As used herein, the term nanoparticle refers to a solid particle of size ranging from 10 to 1000 nm. The 'ideal' nanoparticle is biodegradable, biocompatible, has a size of less than 200 nm and has a rigid biodegradable core into which a substance to be delivered can be incorporated.

The term "microparticle," as used herein, refers to a particle of size ranging from one or greater up to 1000 microns.

The nanoparticles specifically described herein can be fabricated as microparticles if more appropriate for the desired application.

Structure of Particles

Figure 1B:
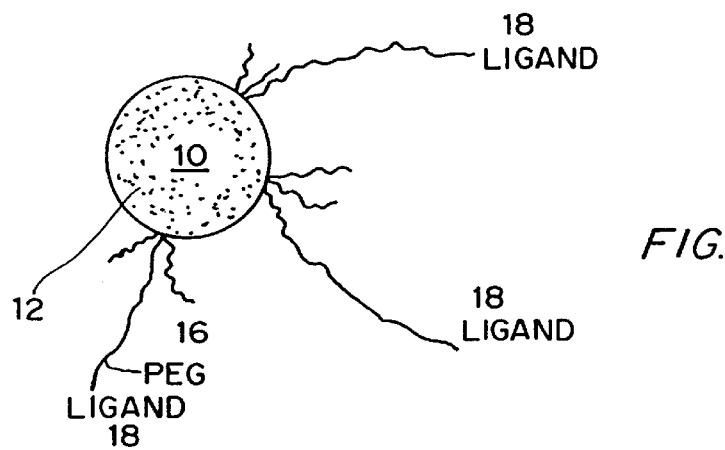
Figure 1C:
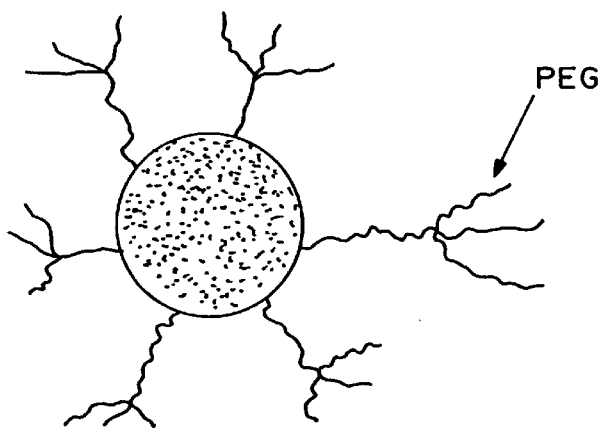

FIGS. 1a, 1b and 1c are schematic representations of embodiments of a nanoparticle prepared as described herein. FIG. 1a, the particle 10 has a biodegradable solid core 12 containing a biologically active material 14, and one or more poly(alkylene glycol) moieties 16 on the surface. The surface poly(alkylene glycol) moieties 16 have a high affinity for water that reduces protein adsorption onto the surface of the particle. The recognition and uptake of the nanoparticle by the reticulo-endothelial system (RES) is therefore reduced. The terminal hydroxyl group of the poly(alkylene glycol) can be used to covalently attach biologically active molecules, as shown in FIG. 1b, or molecules affecting the charge, lipophilicity or hydrophilicity of the particle, onto the surface of the nanoparticle. In FIG. 1c, the PEG is a branched shorter chain PEG molecule than in FIG. 1a.

A nanosphere refers to a nanoparticle that is spherical in shape. The shape of the nanoparticles prepared according to the procedures herein or otherwise known is easily determined by scanning electron microscopy. Spherically shaped nanoparticles are preferred for circulation through the bloodstream. If desired, the particles can be fabricated using known techniques into other shapes that are more useful for a specific application.

Degradation Properties

The term biodegradable or bioerodible, as used herein, refers to a polymer that dissolves or degrades within a period that is acceptable in the desired application (usually in vivo therapy), usually less than five years, and preferably less than one year, on exposure to a physiological solution with a pH between 6 and 8 having a temperature of between 25 and 37° C. In a preferred embodiment, the nanoparticle degrades in a period of between 1 hour and several weeks, depending on the desired application.

Copolymers for the Construction of Nanospheres

The period of time of release, and kinetics of release, of the substance from the nanoparticle will vary depending on the copolymer or copolymer mixture or blend selected to fabricate the nanoparticle. Given the disclosure herein, those of ordinary skill in this art will be able to select the appropriate polymer or combination of polymers to achieve a desired effect.

III. Substances to be Incorporated Onto or Into Particles

Materials to be Delivered

A wide range of biologically active materials or drugs can be incorporated onto or into the particles. The substances to be incorporated should not chemically interact with the polymer during fabrication, or during the release process.

Additives such as inorganic salts, BSA (bovine serum albumin), and inert organic compounds can be used to alter the profile of substance release, as known to those skilled in the art. Biologically-labile materials, for example, procaryotic or eucaryotic cells, such as bacteria, yeast, or mammalian cells, including human cells, or components thereof, such as cell walls, or conjugates of cellular can also be included in the particle. The term biologically active material refers to a peptide, protein, carbohydrate, nucleic acid, lipid, polysaccharide or combinations thereof, or synthetic inorganic or organic molecule, that causes a biological effect when administered in vivo to an animal, including but not limited to birds and mammals, including humans. Nonlimiting examples are antigens, enzymes, hormones, receptors, and peptides. Examples of other molecules that can be incorporated include nucleosides, nucleotides, antisense, vitamins, minerals, and steroids.

Particles prepared according to this process can be used to deliver drugs such as nonsteroidal anti-inflammatory compounds, anesthetics, chemotherapeutic agents, immunotoxins, immunosuppressive agents, steroids, antibiotics, antivirals, antifungals, and steroidal antiinflammatories, anticoagulants. For example, hydrophobic drugs such as lidocaine or tetracaine can be entrapped into the particles and are released over several hours. Loadings in the nanoparticles as high as 40% (by weight) have been achieved. Hydrophobic materials are more difficult to encapsulate, and in general, the loading efficiency is decreased over that of a hydrophilic material.

In one embodiment, an antigen is incorporated into the nanoparticle. The term antigen includes any chemical structure that stimulates the formation of antibody or elicits a cell-mediated humoral response, including but not limited to protein, polysaccharide, nucleoprotein, lipoprotein, synthetic polypeptide, or a small molecule (hapten) linked to a protein carrier. The antigen can be administered together with an adjuvant as desired. Examples of suitable adjuvants include synthetic glycopeptide, muramyl dipeptide. Other adjuvants include killed *Bordetella pertussis,* the liposaccharide of Gram-negative bacteria, and large polymeric anions such as dextran sulfate. A polymer, such as a polyelectrolyte, can also be selected for fabrication of the nanoparticle that provides adjuvant activity.

Specific antigens that can be loaded into the nanoparticles described herein include, but are not limited to, attenuated or killed viruses, toxoids, polysaccharides, cell wall and surface or coat proteins of viruses and bacteria. These can also be used in combination with conjugates, adjuvants, or other antigens. For example, *Haemophilius influenzae* in the form of purified capsular polysaccharide (Hib) can be used alone or as a conjugate with diphtheria toxoid. Examples of organisms from which these antigens are derived include poliovirus, rotavirus, hepatitis A, B, and C, influenza, rabies, HIV, measles, mumps, rubella, *Bordetella pertussus, Streptococcus pneumoniae, C. diphtheria, C. tetani,* Cholera, Salmonella, Neisseria, and Shigella.

Non-pharmaceutical uses for the particles include delivery of food additives, including stabilizers and dispersants or other viscosity modifying agents, controlled and selective delivery of pesticides, herbicides, insecticides, fertilizer, and pheromones, and in color and ink formulations in the printing and ink industry.

Incorporation of Substances for Diagnostic Purposes

In another embodiment, a gamma-labelled nanoparticle is provided that can be used to monitor the biodistribution of the particle in vivo. Any pharmaceutically acceptable gamma-emitting moiety can be used, including but not limited to indium and technetium. The magnetic particles can be prepared as described herein, or alternatively, magnetic nanoparticles, including surface-modified magnetic nanoparticles can be purchased commercially, the surface further modified by attaching the hydrophilic polymeric coating.

For example, the magnetic nanoparticle can be mixed with a solution of the hydrophilic polymer in a manner that allows the covalent binding of the hydrophilic polymer to the nanoparticle. Alternatively, a gamma-emitting magnetic moiety is covalently attached to the hydrophilic or hydrophobic bioerodible polymeric material of the particle. The larger the size of the magnetic moiety, the larger the size of the resulting particles obtained.

Other materials can also be incorporated into the particles for diagnostic purposes, including radiopaque materials such as air or barium and fluorescent compounds. Hydrophobic fluorescent compounds such as rhodamine can be incorporated into the core of the particles. Hydrophilic fluorescent compounds can also be incorporated, however, the efficiency of encapsulation is smaller, because of the decreased compatibility of the hydrophobic biodegradable core with the hydrophilic material. The hydrophilic material must be dissolved separately in water and a multiple emulsion technique used for fabrication of the particle.

In one embodiment, the particles include a substance to be delivered and a multiblock copolymer that is covalently bound to a biologically active molecule, for example, an antibody or antibody fragment, such as the Fab or Fab$_2$ antibody fragments, wherein the particle is prepared in such a manner that the biologically active molecule is on the outside surface of the particle.

Modification of Surface Properties of Particles

The charge, lipophilicity or hydrophilicity of the particle can be modified by attaching an appropriate compound to the hydrophilic polymer on the surface of the particle. The particle can also be coated with a dextran, which are in general more hydrophilic than poly(alkylene glycol) but less flexible. Dextran coated nanoparticles are useful for magnetic resonance imaging (MRI).

Attachment of Specific Ligands to Particle Surfaces

The particles prepared as described herein can be used for cell separation, or can be targeted to specific tissues, by attaching to the surface of the particle specific ligands for given cells in a mixture of cells. When magnetic particles are also incorporated, the particles can be targeted using the ligands, such as tissue specific receptors or antibodies to tissue specific surface proteins, then maintained at the targeted cells using a magnetic field while the particles are imaged or a compound to be delivered is released.

For example, in one embodiment, carmustine (BCNU) or other anti-cancer agent such as cis-platin is incorporated in the core of the particles and antibodies to the target cancerous cells are covalently bound to the surface of the particle.

Pharmaceutical Administration of Nanospheres

The particles described herein can be administered to a patient in a variety of routes, for example, orally, parenterally, intravenously, intradermally, subcutaneously, or topically, in liquid, cream, gel or solid form.

The particles can be lyophilized and then formulated into an aqueous suspension in a range of microgram/ml to 100 mg/ml prior to use. Alternatively, the particles can be formulated into a paste, ointment, cream, or gel, or transdermal patch.

The nanoparticle should contain the substance to be delivered in an amount sufficient to deliver to a patient a therapeutically effective amount of compound, without causing serious toxic effects in the patient treated. The desired concentration of active compound in the nanoparticle will depend on absorption, inactivation, and excretion rates of the drug as well as the delivery rate of the compound from the nanoparticle. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions.

The particles can be administered once, or may be divided into a number of smaller doses to be administered at varying intervals of time, depending on the release rate of the particle, and the desired dosage.

IV. Coatings of Implantable Devices

Polymers loaded as described herein can also be used to coat implantable devices, such as stents, catheters, artificial vascular grafts, and pacemakers. The device can be coated with the lyophilized powder of the particles, or otherwise as known to those skilled in the art. The coating can release antibiotics, anti-inflammatories, or anti-clotting agents at a predetermined rate, to prevent complications related to the implanted devices. Controlled delivery devices prepared as described herein can also be used as ocular inserts for extended release of drugs to the eye.

EXAMPLES

The preparation of specific multiblock copolymers of hydrophobic bioerodible polymers such as PLA and PLGA, and hydrophilic polyalkylene glycols such as PEG, with multifunctional compounds such as tartaric acid, mucic acid, citric acid, benzene tetracarboxylic acid, glucaronic acid, and butane diglycidyl ether are described in detail below. These polymers were prepared with PEG of various chain lengths, and with various hydrophobic polymers. Given this detailed description, one of skill in the art will know how to produce a wide variety of multiblock copolymers suitable for fabrication into nanospheres.

Materials and Methods.

Low toxicity stannous octoate was purchased from ICN. D,L-lactide was purchased from Aldrich Chemical Company, and glycolide from Polysciences, Inc. These compounds were recrystallized before use from ethyl acetate. High purity monomethoxy PEG (M-PEG) with molecular weight 5,000, 12,000 and 20,000 was purchased from Shearwater Polymers, Inc. The number average molecular weight of the polymer was determined with on a Perkin-Elmer GPC system with an LC-25 refractive index detector equipped with a mixed bed Phenogel column filled with 5 $\mu$m particles from Phenomenex. Chloroform was used as the eluent, with a flow rate of 0.9 ml/min. The molecular weights were determined relative to narrow molecular weight polystyrene and poly(ethylene glycol) standards from Polysciences.

Thermal transition data was collected with a Perkin-Elmer DSC-7 (Newton Center, Mass.). The sample weight ranged from 20 to 25 mg. Indium was used for temperature and enthalpy calibrations. Each sample was subjected to a heat-cool-heat cycle from −60 to 150° C. with a rate of 10° C./min. Wide angle x-ray diffraction spectra were obtained with a Rigaku Rotaflex Diffractometer from Rigaku Corporation (Danvers, Mass.) with S=0.05 using a Nickel filtered Cu K$\alpha$ source. The data was analyzed on a Micro Vax II computer. The IR spectra were recorded on a Nicolet 500 spectrometer using a polymer powder melted on sodium chloride crystals to obtain thin films. $^{13}$C NMR studies were conducted on samples dissolved in deuterated chloroform with a Nicolet NT-360 spectrometer. Peak fitting was carried out with a VG data system.

Example 1

Synthesis of (Methoxy-PEG-NH$_2$)$_3$, Citrate (Compound A)

Three PEG citrates were prepared as follows:

PEG-NH$_2$ (1 gram, MW=5,000, Sherewater) was reacted with citric acid (14 mg, 0.33 equivalents) using dicyclohexylcarbodiimide (DCC) (54 mg, 1 equivalent) and DMAP (4 mg, catalyst) in 10 ml of dry dichloromethane. The reaction was continued for 2 days at room temperature with magnetic stirring. The DCU by-product was isolated by filtration and the filtrate was poured into 100 ml of ether-:petroleum ether 1:1 mixture. The precipitated polymer was washed with ether and dried to yield 0.8 grams of a white powder. The product did not contain acid groups (Bromophenol test) and showed a single peak at the GPC chromatogram in the area of 15,000. IR showed typical ester peak (1720 cm$^{-1}$). Methoxy-PEG citrate trimers with PEG of the following molecular weights, 1,900; 12,000; and 20,000 were prepared using this procedure.

The PEG derivatives of tartaric acid [(methoxy-PEG)2-tartrate], mucic acid [(methoxy-PEG)-2-mucoate], and glucaronic acid (methoxy-PEG-mucoate) with various PEG chain length were prepared similarly. All derivatives possessed the appropriate molecular weight (determined by GPC using PEG standards), showed a negative result in the bromophenol test for carboxylic acids, and had an absorption peak at 1720 typical for amide bonds.

Example 2

Esterification Reaction Between Methoxy PEG-OH and Citric Acid Using DCC

The reaction conditions were the same as above, and an 80% conversion was obtained, as determined by GPC (compound A-1)

Example 3

Direct Esterification Reaction Between Methoxy PEG-OH and Citric Acid

In a 100 ml round bottom flask equipped with a Dean-Stark azeotrope apparatus, methoxy PEG-OH (MW 1900, Polysciences) was reacted with citric acid (0.33 equivalents) in toluene and sulfuric acid as catalyst (1%). The reaction was conducted under reflux using azeotrope for H$_2$O removal. About 75% yield was obtained as determined by GPC.

Example 4

Trans Esterification Reaction Between Methoxy PEG-OH and Methyl Citrate Ester

Citrate methyl ester was obtained from the reaction between citric acid and access methanol at reflux.

The resulting trimethyl citrate (1 equivalent) was reacted with methoxy PEG Mw-1900 (3 equivalents) in refluxing toluene for three hours. The product was isolated in about 70% yield, as determined by GPC, after evaporation of the toluene and extraction with diethyl ether.

Example 5

Synthesis of: (PEG)$_3$-citrate-polylactide [PEG$_3$-PLA] or PEG$_3$-caprolactone [PEG$_3$-PCL] Diblock Copolymers (Compound A1, FIG. 2a)

PEG$_3$-citrate (1 gram) (Sherewater, MW-5,000, 12,000, and 20,000) was dissolved in 20 ml benzene. Lactide (5 grams) (Aldrich, 99%+) was added and the solution was allowed to reflux and azeotrope for 60 min. Stannous octoate (0.2% by weight (per lactide)) was added as a 1% solution in benzene. The reaction was refluxed for 5 hours, the solvent was removed azeotropically and a viscous material was obtained. The polymerization was continued for 2 hours at 130° C. The resulting polymer was a clear, slightly yellow mass, and showed a high molecular weight (Table 1). The multiblock copolymers of PEG-polycaprolactone were similarly synthesized. The polymers were soluble in common organic solvents.

TABLE 1

Molecular weights of PEG block copolymers

| Polymer MP | | Mn | Mw |
|---|---|---|---|
| PEG-PCL block copolymers | | | |
| PCL-PEG 5k (1:5 w/w) | 29,500 | 70,100 | 55–58 |
| PCL-PEG 12k (1:5 w/w) | 25,500 | 88,100 | 55–58 |
| PCL-PEG 20k (1:5 w/w) | 34,500 | 105,900 | 50–56 |
| PEG-citrate-PLA multiblock copolymers | | | |
| (PEG-NH 5k)$_3$ citrate | 15,600 | — | |
| (PEG-NH 5k)$_3$ citrate-PLA | 71,900 | 228,100 | 65–75 |
| (PEG-NH 5k)$_3$ citrate-PCL | 42,000 | 170,000 | 52–58 |
| PSA-PEG block copolymers | | | |
| PSA-COO-PEG 5k (3:1 w/w) | 19,500 | 119,100 | 65–78 |
| PSA-COO-PEG 12k (3:1 w/w) | 21,000 | 144,200 | 65–78 |
| PSA-COO-PEG 20k (3:1 w/w) | 18,500 | 105,000 | 65–78 |
| P(SA-PEG 5k) random block (1:3) | 21,000 | 105,400 | 64–73 |
| PSA | 17,200 | 81,300 | 80–82 |
| P(FAD)-COO-PEG 5k (3:1) | 12,000 | 34,000 | 42–48 |
| P(CPP-SA)1:1-COO-PEG 5k (3:1) | 12,000 | 34,000 | 42–48 |

Example 6

Synthesis of Multiblock (Brush) PEG-ligand-PLA (Compound B, FIG. 2a)

Citric acid (0.1 mole) was reacted with a mixture of methoxy-PEG amine (MW 1900) (0.2 mole) and benzyl ester carboxy-PEG-amine (MW 5,000) (0.1 mole) using DCC (0.33 equivalents) and DMAP (0.01 mole, catalyst) in 100 ml of dry dichloromethane. The reaction was continued for 2 days at room temperature with magnetic stirring. The DCU by-product was isolated by filtration and the filtrate was poured into 500 ml of ether:petroleum ether 1:1 mixture. The precipitated polymer was washed with ether and dried to yield a white powder in 90% yield. The product did not contain acid groups (Bromophenol test) and showed a single peak at the GPC chromatogram with a molecular weight of 9,000. IR showed typical ester peak (1720 cm$^{-1}$). Block copolymers with lactide and caprolactone were synthesized using the same method described for PLA-PEG brush block copolymers.

The PLA-PEG citrate trimer was dissolved in tetrahydrofuran and hydrogenated with Hydrogen-Palladium catalysis to remove the benzylic protecting group at the PEG 5000 chain. The end chain carboxylic acid PEG was then reacted with bovine serum albumin (representing a ligand) using DCC as an activating agent for amide coupling.

Similarly, two or three ligands can be attached to (PEG) 3-citrate by using two or three equivalents of benzyl carboxylate-terminated PEG-amines, using the above method.

Example 7

Figure 2B:
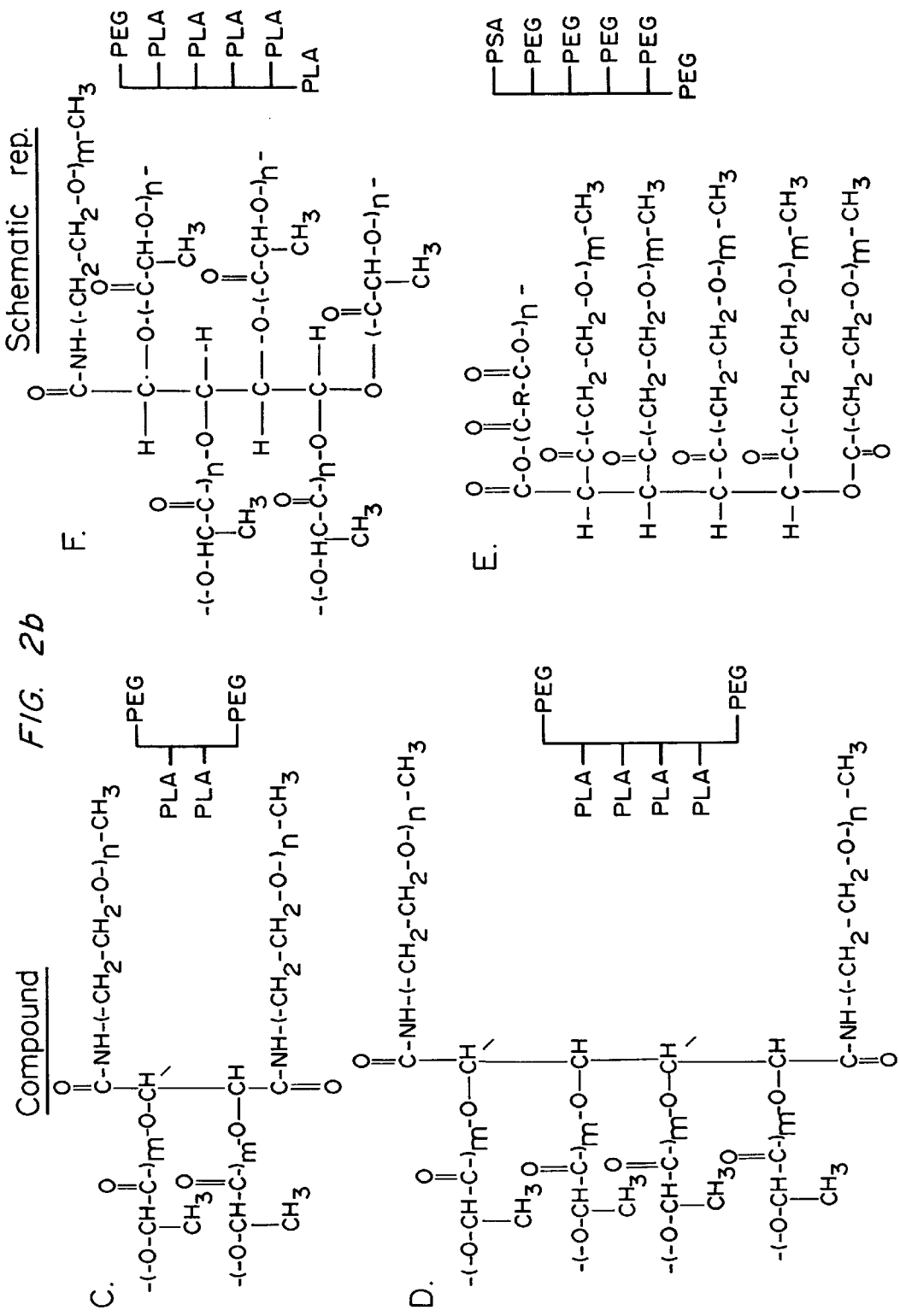
FIG. 2b is a schematic illustration of multiblock copolymers of tartaric acid and mucic acid with polylactic acid (PLA), polycaprolactone (PCL), polysebacic acid (PSA) and polyglycolic acid (PGA) hydrophobic blocks, and polyethylene glycol (PEG) hydrophilic blocks.

Preparation of PEG$_2$-tartrate-PLA$_2$ (Compound C, FIG. 2b)

Di-PEG tartrate was prepared from the reaction between amino terminated methoxy PEG and tartaric acid with DCC as the activating agent, using the procedure described for the synthesis of (PEG)$_3$-citrate. The di-PEG tartrate derivative was reacted with lactide or glycolide mixtures to form clear polymers (Table 1).

Example 8

Preparation of Di-methoxy PEG-mucoate-tetra PLA (Compound D, FIG. 2b)

Mucic acid (Aldrich) was reacted with two equivalents of methoxy PEG in the presence of DCC in DMF to form di-PEG-mucoate which was copolymerized with lactide, glycolide or caprolactone to form high molecular weight (Mw=65,000–95,000) hexa-armed block copolymers.

Example 9

Preparation of Penta-methoxy PEG-glucoronate-anhydride (Compound E, FIG. 2b)

Glucaronic acid was reacted with carboxylic acid terminated methoxy PEG (NW=5,000, Sherewater) in the presence of DCC to form (PEG)$_5$-gluconate. The penta-PEG compound was polymerized with sebacic acid (1:5 weight ratio) using acetic anhydride as a dehydrating agent. Polymers with a molecular weight of approximately 75,000 were obtained.

Example 10

Preparation of Mono-PEG-penta PLA Glucoronate (Compound F, FIG. 2b)

Glucaronic acid was reacted with amino terminated methoxy PEG (MW=5,000, Sherewater) in the presence of DCC in dichloromethane of DMF to form PEG-gluconate amide. The gluconate PEG derivative was polymerized with lactide, glycolide or caprolactone (1:5 weight ratio).

Example 11

Figure 2C:
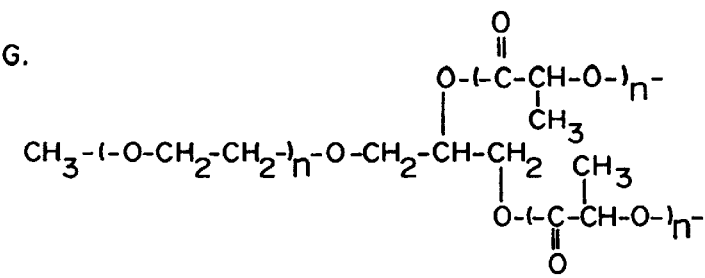
FIG. 2c is a schematic illustration of PEG-di-PLA.
Figure 2C:
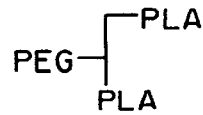

Preparation of PEG-di-PLA (Compound G, FIG. 2c)

Methoxy-PEG-epoxide terminated (Sherewater) was hydrolyzed in a sodium carbonate solution overnight at room temperature. The resulted PEG with two hydroxyl groups was isolated by precipitation in ether:methanol 1:1 mixture and dried. The dihydroxy-terminated PEG was block copolymerized with lactide, glycolide and caprolactone to form high molecular weight polymers (The molecular weight was in the range of 70,000 to 115,000).

Example 12

Preparation of Trimethoxy PEG-citrate-poly (Sebacic Anhydride) Diblock Copolymer (Compound H, FIG. 2a)

Trimethoxy-PEG-citrate (0.01 mole, prepared as above) reacted with access adipoyl chloride (0.012 mole) in dichloromethane with triethylamine as a proton acceptor. After 24 hours at room temperature, water was added, the reaction mixture was stirred at room temperature for one hour, and the polymer was isolated by the adding a mixture of methanol-diethyl ether 1:1. The resulting trimethoxy-PEG-citrate-adipate was reacted with acetic anhydride to form the acetate anhydride derivative, which was polymerized with a sebacic anhydride prepolymer to form a multiblock copolymer with a molecular weight of Mw=58,000; Mn=31,000. MP=65–74° C.

Example 13

Figure 2D:
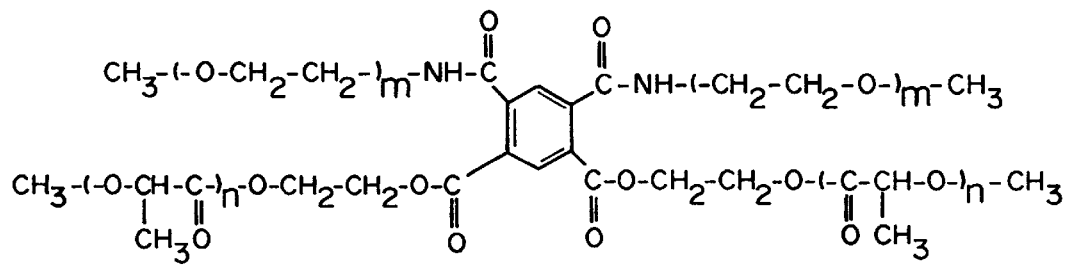
FIG. 2d is a schematic illustration of multiblock copolymers of benzene tetracarboxylic acid with polyethylene glycol (PEG) and polylactic acid (PLA) or polysebacic anhydride (PSA) blocks.
Figure 2D:
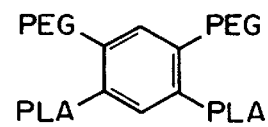
Figure 2D:
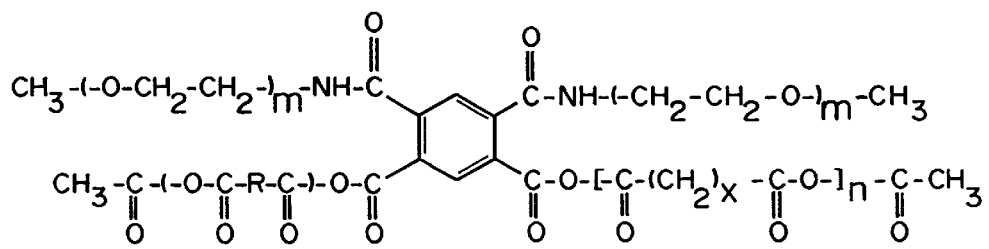
Figure 2D:
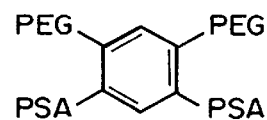

Benzene Tetracarboxylic Anhydride (BTCA) Derivatives (Compound I, FIG. 2d)

BTCA was reacted with two equivalents of methoxy PEG amine in refluxing THF for 5 hours to yield dimethoxy-PEG tetracarboxybenzoate, with two remaining carboxylic groups. The PEG-dimer was reacted with acetic anhydride and then with sebacic anhydride to form the tetra-armed diblock PEG$_2$-benzene-PSA$_2$.

Alternatively, polycaprolactone diol (Mw-3,000, Polysciences) was reacted with dimethoxy-PEG tetracarboxybenzoate containing 2 carboxylic acids to form the tetra-armed PEG-PCL diblock copolymer. The PLA or PCL block copolymers were prepared, and then the carboxylic acid groups of the PEG-benzene tetracarboxylate were reacted with propylene oxide to form the hydroxyl derivative available for the block copolymerization with lactide, glycolide and caprolactone.

Example 14

Figure 2E:
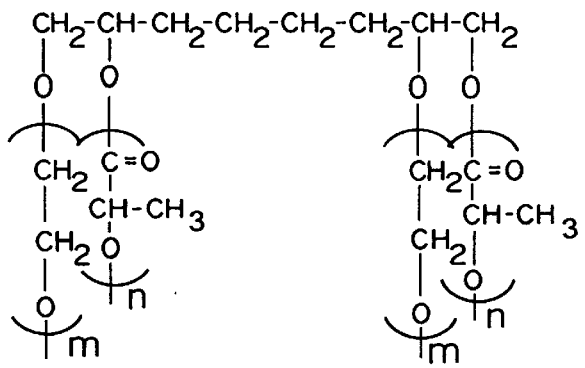
FIG. 2e is a schematic illustration of the synthesis of butane diglycidyl ether-based tetra-arm diblock copolymers with polylactic acid (PLA) and polyethylene glycol (PEG) blocks.

Butane Diglycidyl Ether Based Tetra-Arm Diblock Copolymers (Compound J. FIG. 2e)

Butane diglycidyl ether was reacted with two equivalents of methoxy-PEG-OH in refluxing THF for 10 hours. The PEG dimer was block copolymerized with lactide, glycolide or caprolactone in toluene with stannous octoate as catalyst. High molecular weight polymers were obtained (Please define high molecular weight).

Example 15

Figure 2F:
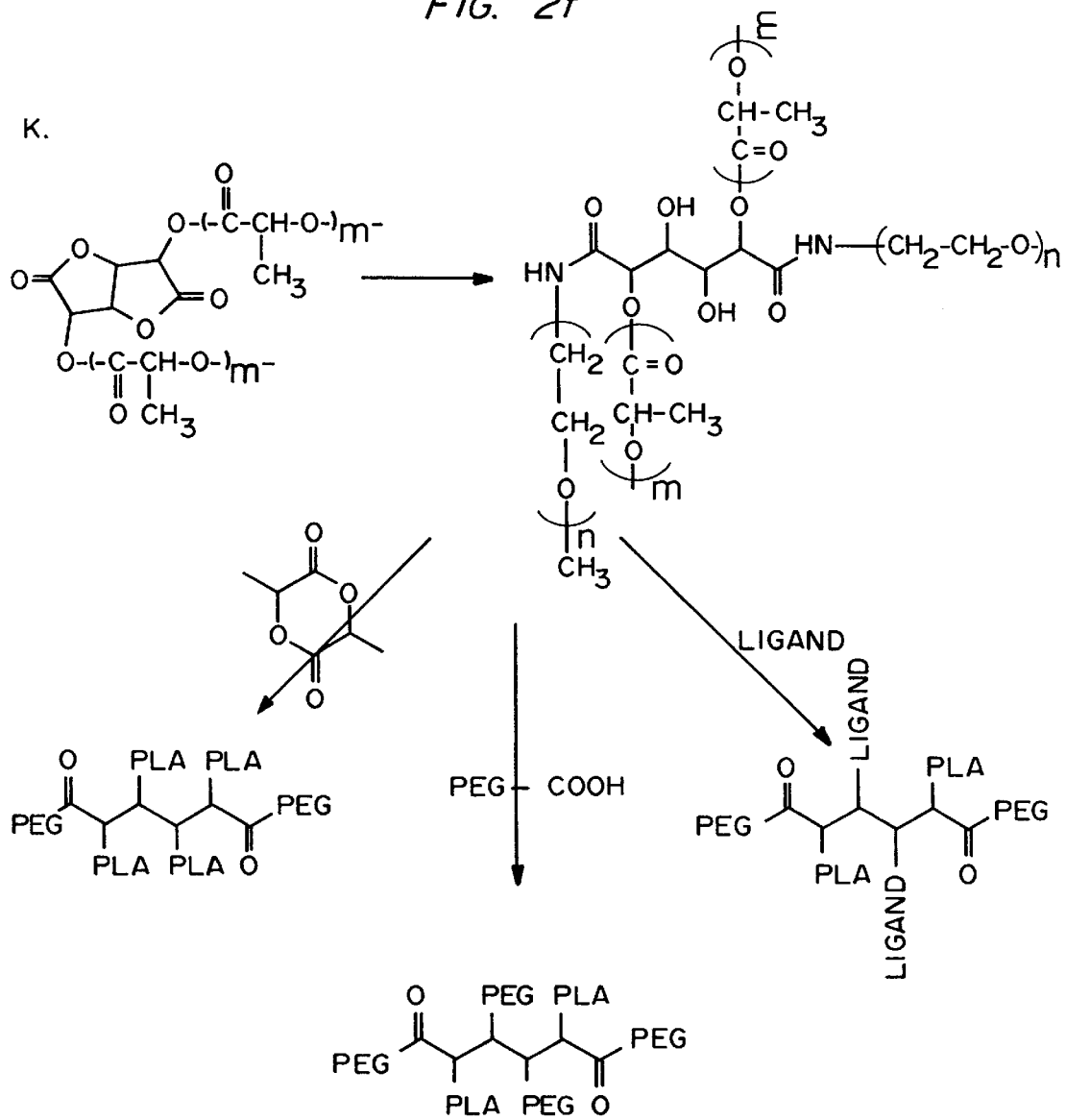
FIG. 2f is a schematic illustration of multiblock copolymers of the 1,4-3,6-dilactone of glucaric acid with ligand, polylactic acid (PLA) and polyethylene glycol (PEG) blocks.
Figure 2G:
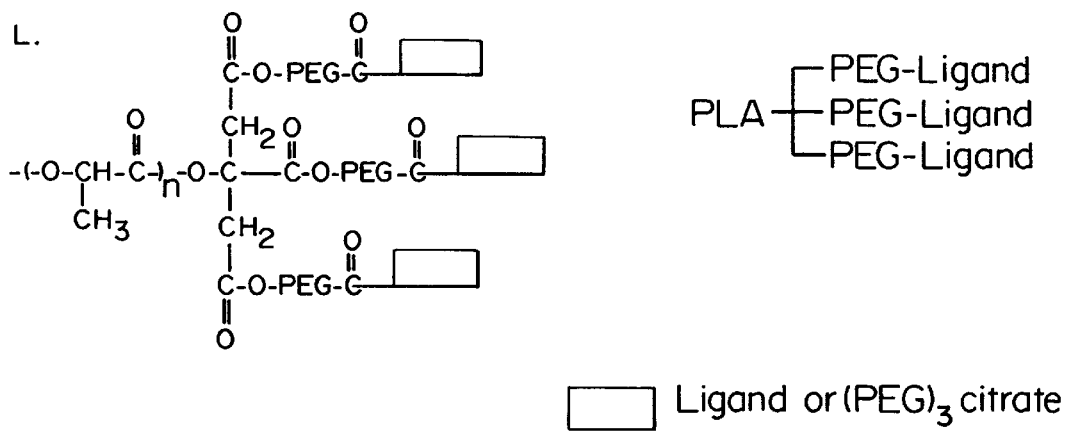
FIG. 2g is a schematic illustration of (PEG)$_3$-citrate-polylactide in which the PEG blocks are further functionalized with a ligand or PLA.
Figure 2G:
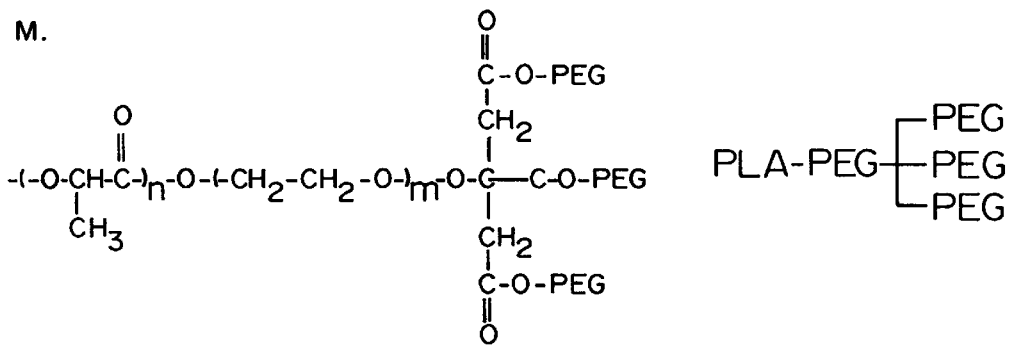

Multiblock Copolymers Based on the 1,4;3,6-Dilactone of Glucaric Acid (Compound K, FIG. 2f)

PLA was polymerized in the presence of the dilactone (5:1 weight ratio) using stannous octoate as catalyst in benzene. The two carboxylic acid groups were used to attach methoxy-PEG-amine via an amide bond.

Example 16

Figure 2H:
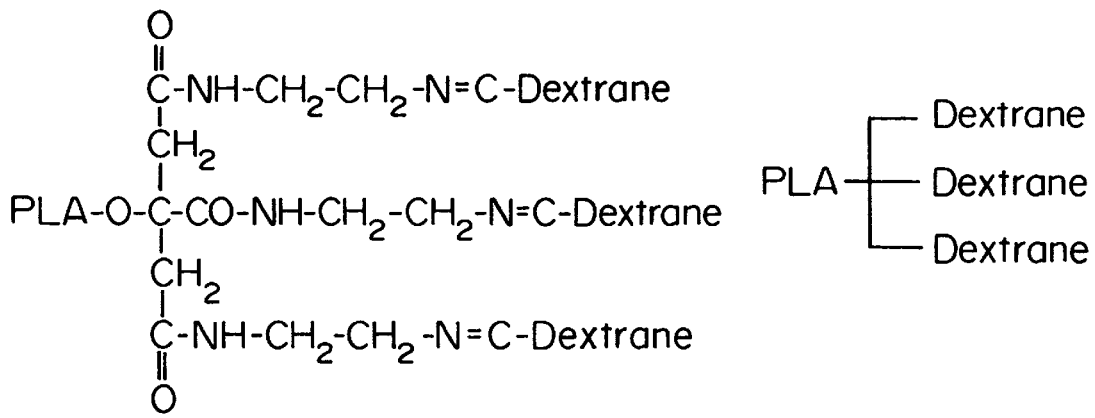
FIG. 2h is a schematic illustration of PLA-citrate-dextran and PLA-2-hydroxyadipaldehyde-Dextran.
Figure 2H:
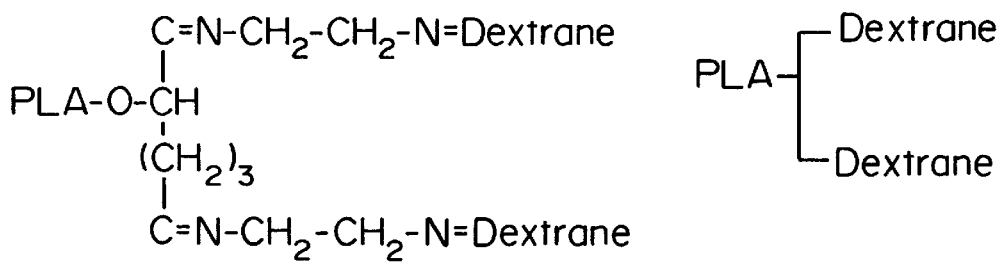

Synthesis of PLA-citrate-dextran (Compound N, FIG. 2h)

Dextran, a clinically used biodegradable material, was used as alternative hydrophilic polymer to PEG. The benzyl ester of citric acid was polymerized with lactide to form a PLA-terminated citrate ester which was hydrogenated to remove the benzyl groups. The citric acid terminated-PLA was esterified with dextran to form PLA-citrate-Dextran$_3$

Example 17

Figure 2I:
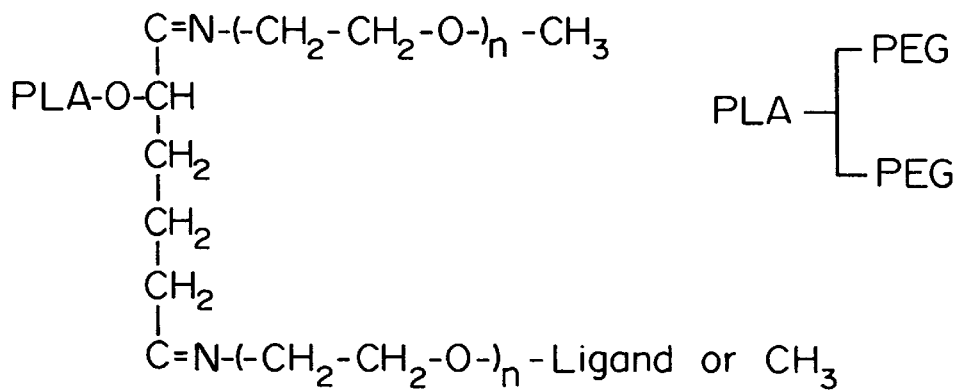
FIG. 2i is a schematic illustration of PEG 2-hydroxyadipaldehyde-PLA in which the PEG can be functionalized with a ligand or a methyl group.

Derivatives of PEG 2-Hydroxyadipaldehyde (Compound M, FIG. 2i)

2-Hydroxyadipaldehyde (Aldrich) was reacted with amino terminated PEG to form the Schiff base which was hydrogenated with NaBH$_4$ to form the corresponding amine. The di-PEG derivative was reacted with lactide or caprolactone in the presence of stannous octoate to form the PLA or PCL-PEG$_2$ diblock copolymer.

Example 18

Derivatives of Dextran or Ligand 2-Hydroxyadipaldehyde (Compound M-1, FIG. 2h)

2-Hydroxyadipaldehyde is reacted with lactide in the presence of stannous octoate to form adipaldehyde-terminated PLA. The aldehyde groups are reacted with animo side groups of a ligand (peptide or protein) to form a di-ligand-PLA diblock. Alternatively, the aldehydic terminals are reacted with ethylene diamine to form PLA-terminated with diamino groups. This polymer is reacted with an oxidized polysaccharide, such as dextran or amylose, to form a PLA-di-(polysaccharide) derivative.

Example 19

Polyanhydride-PEG

Polyanhydride-terminated PEG was prepared by melt condensing a sebacic acid prepolymer (synthesized by refluxing sebacic acid in acetic anhydride and precipitating the resulting polymer in ether/petroleum ether solution) and methoxy PEG-OH or methoxy PEG-carboxylate acetate anhydride. In a typical experiment, methoxy-PEG-carboxylate (1 gram) was mixed with sebacic acid prepolymer (3 grams). The mixture was polymerized at 180° C. under vacuum (0.1 mm Hg) for 90 minutes to yield the polymer. The polymer showed IR absorption at 1805 and 1740 cm−1 (typical for aliphatic anhydride bonds), and the $^1$H-NMR spectrum fit the polymer structure.

Example 20

Preparation of Nanoparticles from Mixtures of Non-Linear Multiblock Copolymers and Linear Polymers and Copolymers Nanospheres were prepared from a mixture of $PEG_3$-citrate-PLA, a PLGA-PEG copolymer and a polycaprolactone homopolymer in a ratio of 1:1:3 by weight, using an emulsion/evaporation technique as described above. The pre-formed polymers were dissolved in an organic solvent (Which solvent) at a concentration of (What concentration?) polymer/solvent. The resulting organic solution was emulsified with an aqueous phase by vortexing and then sonicated for 1 minute at 40-W output. The solvent was evaporated and the nanospheres were collected by centrifugation (30 min, 5,000 rpm), washed twice and lyophilized, yielding nanospheres with an average size of approximately 200 nm.

Example 21

Drug Release Characteristics

Lidocaine and prednisolone (Sigma), were selected for encapsulation because of their low water solubility (less than 5 mg/mL in water), high solubility in organic solvents (more than 20 mg/mL in organic solvents such as chlorinated hydrocarbons, tetrahydrofuran, dimethyl formamide or dioxane) and ease of detection by UV spectrophotometry.

Release tests were carried out with nanospheres loaded with lidocaine in different amounts (20% wt, 33% wt), in phosphate buffer solution (PBS, pH 7.4) at 37° C. A dialysis membrane (50,000 cut-off) was filled with a suspension of lyophilized nanospheres (10 mg/5 ml PBS) and then placed into 25 ml of PBS. Samples were taken from the outer solution, then replaced every time with fresh ones. Drug released was detected spectrophotometrically at 240 nm.

While high encapsulation efficiency can be achieved with particles made from multiblock brush copolymers, it can be difficult to obtain 100% encapsulation efficiency due to the hydrophilicity of the multiblock copolymers. It was observed that the encapsulation efficiency can be less than 70% for $PEG_3$-citrate-PLA multiblock copolymers with a PEG (m.w. of 5, 12, 20 kDa).

In vitro studies were performed to investigate the release characteristics of PEG-coated nanospheres, in particular to study the effect of the presence of PEG on the nanosphere surface and the effect of the nanosphere core composition (polymer and drug nature, drug loading) on the drug release kinetics. Suspensions of nanospheres were easily obtained by redispersing freeze-dried particles in aqueous solutions by vortexing, without any further additives. Lidocaine was used as a model drug. The release of lidocaine was studied in particles made from linear PEG-PGLA copolymers as well as non-linear brush copolymers.

Both types of particles show a continuous release in vitro over several hours, but have different release kinetics. The molecular weight does not effect the release pattern of PEG-PLGA nanospheres, since the drug is completely released in about ten hours using copolymers with a PEG m.w. of 5, 12, 20 KDa. The presence of PEG on the surface of the nanospheres is not expected to modify the drug release. However, with multiblock copolymers, factors such as higher PEG density and PEG chain length can slow down drug release. In ten hours, more than 90% of lidocaine was released from PLA nanospheres, but only 60% from (PEG $20K)_3$-PLA particles.

Drug release from nanospheres made from PEG-$\epsilon$-polycaprolactone is biphasic.

Because of polymer erosion, it would ordinarily be expected that a core made of polyanhydride should lead to a faster drug release. However, after an initial fast release in the first two hours, drug release reached a plateau, although drug was released at a constant rate for an additional eight hours.

Polymer degradation kinetics were also investigated in vitro. With PEG-PLGA, PEG-PCL and $(PEG)_3$-PLA particles, the polymers start to degrade after weeks. Nanosphere cores made of polyanhydrides start to degrade immediately. In the first case, drug release is governed by a diffusion mechanism, since the drug can be completely released before polymer degradation occurs. With polyanhydrides, polymer erosion affects drug release, and drug characteristics have a more important role in release kinetics. The particle's small size and large surface area increases the rate of polymer erosion relative to other drug delivery systems, such as slabs, and afterwards drug solubility governs the dissolution kinetics.

The amount of drug loading can have a strong effect on the release kinetics. PEG-PLGA nanospheres containing 33% wt of lidocaine can release the drug for over 12 hours. Surprisingly, particles loaded with 10% of the drug can show complete drug release in 6 hours. Increased drug loading can cause part of the drug loaded in the core to recrystallize, as shown by DSC. The presence of crystals of a hydrophobic drug, such as lidocaine, can slow down the release kinetics. ESCA studies performed on drug loaded nanospheres confirmed that drug crystals were not located on the nanosphere surface. The polymer composition was also modified and the drug loading was increased up to 45% wt.

Example 22

Evaluation of Biodistribution of $^{111}$In-labeled Nanoparticles in Vivo

Indium 111 ("In") can be directly attached to the multiblock copolymer chains by complex formation. In and diethyltriamiopentaacetic acid (DTPA) are reacted with stearylamine. The resulting compound, In-DTPA-stearylamide, is hydrophobic enough to interact to be encapsulated within the hydrophobic core. In this case, the molecular weights of the hydrophilic and hydrophobic polymers have little effect on the interaction. After incubation at 37° C. in PBS or horse serum for more than 24 hours, label loss can be assessed by measuring the radioactivity of the supernatant solutions after centrifugation. This labelling method can therefore be useful for in vivo studies, by gamma-scintography or by direct measurement of the radioactivity in the blood and/or different organs.

This invention has been described with reference to its preferred embodiments. Variations and modifications of the invention will be obvious to those skilled in the art from the foregoing detailed description of the invention. It is intended that all of these variations and modifications be included within the scope of the appended claims.

We claim:

1. Multiblock copolymers comprising a multifunctional compound covalently linked to at least three polymer blocks, wherein the polymer blocks comprise one or more hydrophilic polymers and one or more hydrophobic bioerodible polymers.

2. The multiblock copolymer of claim 1 wherein the multifunctional compound is selected from the group consisting of dextrins, pentaerythritol, glucaronic acid, tartaric acid, mucic acid, citric acid, benzene tricarboxylic acid, benzene tetracarboxylic acid and butane diglycidyl ether.

3. The multiblock copolymer of claim 1 wherein the hydrophilic polymer is selected from the group consisting of polyalkylene glycols, polyvinyl alcohols, polypyrrolidones, poly(amino acids), oxidized cellulose and dextrans.

4. The multiblock copolymer of claim 3 wherein the poly(amino acids) are selected from the group consisting of gelatin, fibrinogen and albumin fragments.

5. The multiblock copolymer of claim 1 wherein the hydrophobic polymer is selected from the group consisting of polyphosphazenes, polyphosphate esters, polyanhydrides, polyhydroxybutyric acid, polyorthoesters, polycaprolactone, poly($\alpha$-hydroxy acids), polybutylene glycol and copolymers prepared from the monomers of these polymers.

6. A particle having a diameter of between 50 nm and 1000 $\mu$m formed of or coated with a multiblock copolymer formed by covalently linking a multifunctional compound to at least three polymer blocks, wherein the polymer blocks comprise one or more hydrophilic polymers and one or more hydrophobic bioerodible polymers to form a coblock polymer.

7. The particle of claim 6 further comprising a substance to be delivered selected from the group consisting of peptides, proteins, carbohydrates, nucleic acids, lipids, polysaccharides, combinations thereof, and synthetic inorganic or organic molecules that cause a biological effect when administered to an animal.

8. The particle of claim 6 wherein the hydrophilic polymer is selected from the group consisting of polyalkylene glycols, polyvinyl alcohols, polypyrrolidones, poly(amino acids), oxidized cellulose and dextrans.

9. The particle of claim 8 wherein the poly(amino acid) is selected from the group consisting of gelatin, fibrinogen and albumin fragments.

10. The particle of claim 8 wherein the polyalkylene glycol is selected from the group consisting of polyethylene glycol and polyoxyethylene/polyoxypropylene copolymers.

11. The particle of claim 6 wherein the hydrophobic polymer is selected from the group consisting of polyphosphazenes, polyphosphate esters, polyanhydrides, polyhydroxybutyric acid, polyorthoesters, polycaprolactone, poly($\alpha$-hydroxy acids) and copolymers prepared from the monomers of these polymers.

12. The particle of claim 6 wherein the multifunctional compound is selected from the group consisting of dextrins, pentaerythritol, glucaronic acid, tartaric acid, mucic acid, citric acid, benzene tricarboxylic acid, benzene tetracarboxylic acid and butane diglycidyl ether.

13. The particle of claim 6 comprising molecules covalently bound to the surface of the particle via reactive groups on the hydrophilic polymer, wherein the molecules are selected from the group consisting of biologically active molecules, non-biologically active molecules which can be detected, targeting molecules, and molecules affecting the charge, lipophilicity or hydrophilicity of the particle.

14. The particle of claim 13, wherein the targeting molecule is selected from the group consisting of compounds specifically reactive with a cell surface component, antibodies and antibody fragments.

15. The particle of claim 6 wherein the diameter is less than one micron.

16. The particle of claim 6 wherein the diameter is between one and 1000 microns.

17. The particle of claim 13 wherein the detectable molecule is selected from the group consisting of substances detectable by x-ray, fluorescence, ultrasound, magnetic resonance imaging and radioactivity.

18. The particle of claim 8, wherein the poly(alkylene glycol) is poly(ethylene glycol).

19. The particle of claim 6 formed of a core of a different material than the coblock polymer coating.

20. A method for making a multiblock copolymer by covalently linking a multifunctional compound to at least three polymer blocks, wherein the polymer blocks comprise one or more hydrophilic polymers and one or more hydrophobic bioerodible polymers.

21. The method of claim 20 further comprising forming a particle with a diameter between 50 nm and 1000 $\mu$m of the coblock polymer or coating a particle with a diameter between 50 nm and 1000 $\mu$m with the coblock polymer.

22. The method of claim 21 further comprising incorporating a substance in the particle.

23. The method of claim 22 wherein the substance is a biologically active substance selected from the group consisting of peptides, proteins, carbohydrates, nucleic acids, lipids, polysaccharides, combinations thereof, and synthetic inorganic or organic molecules that cause a biological effect when administered in vivo to an animal.

24. The method of claim 20 wherein the hydrophilic polymer is selected from the group consisting of polyalkylene glycols, polyvinyl alcohols, polypyrrolidones, poly (amino acids), oxidized cellulose and dextrans.

25. The method of claim 24 wherein the poly(amino acid) is selected from the group consisting of gelatin, fibrinogen and albumin fragments.

26. The method of claim 20 wherein the hydrophobic polymer is selected from the group consisting of polyphosphazenes, polyphosphate esters, polyanhydrides, polyhydroxybutyric acid, polyorthoesters, polycaprolactone, poly($\alpha$-hydroxy acids) and copolymers prepared from the monomers of these polymers.

27. The method of claim 20 wherein the multifunctional compound is selected from the group consisting of dextrins, pentaerythritol, glucaronic acid, tartaric acid, mucic acid, citric acid, benzene tricarboxylic acid, benzene tetracarboxylic acid and butane diglycidyl ether.

28. The method of claim 21 further comprising covalently binding to the surface of the particle via the terminal hydroxyl group of the poly(alkylene glycol) molecules selected from the group consisting of biologically active molecules, non-biologically active molecules which can be detected, targeting molecules, and molecules affecting the charge, lipophilicity or hydrophilicity of the particle.

29. The method of claim 28 further comprising targeting the particle for delivery to a specific cell type by attaching to the surface of the particle a targeting molecule selected from the group consisting of compounds specifically reactive with a cell surface component, antibodies and antibody fragments.

30. The method of claim 28 wherein the molecule is a substance detectable by x-ray, fluorescence, magnetic resonance imaging, ultrasound or radioactivity.

31. A method for delivering a substance to a patient comprising administering to the patient a particle having a diameter of between 50 nm and 1000 μm, wherein the particle is formed of or is coated with a multiblock copolymer, the multiblock copolymer comprises a multifinctional compound covalently bound to at least three polymer blocks, wherein the polymer blocks comprise one or more hydrophilic polymers and one or more hydrophobic bioerodible polymers.

32. The method of claim 31 wherein the substance to be delivered is a biologically active substance selected from the group consisting of peptides, proteins, carbohydrates, nucleic acids, lipids, polysaccharides, combinations thereof, synthetic inorganic molecules that cause a biological effect when administered to an animal and synthetic organic molecules that cause a biological effect when administered to an animal.

33. The method of claim 31 wherein the hydrophilic polymer is selected from the group consisting of polyalkylene glycols, polyvinyl alcohols, polypyrrolidones, poly (amino acids), oxidized cellulose and dextrans.

34. The method of claim 33 wherein the polyalkylene glycol is selected from the group consisting of polyethylene glycol and polyoxyethylene/polyoxypropylene copolymers.

35. The method of claim 31 wherein the hydrophobic polymer is selected from the group consisting of polyphosphazenes, polyphosphate esters, polyanhydrides, polyhydroxybutyric acid, polyorthoesters, polycaprolactone, poly(α-hydroxy acids) and copolymers prepared from the monomers of these polymers.

36. The method of claim 31 wherein the multifunctional compound is selected from the group consisting of dextrins, pentaerythritol, glucaronic acid, tartaric acid, mucic acid, citric acid, benzene tricarboxylic acid, benzene tetracarboxylic acid and butane diglycidyl ether.

37. The method of claim 22 further comprising delivering a substance to a patient comprising administering the particle to the patient, wherein the substance to be delivered is a biologically active substance selected from the group consisting of peptides, proteins, carbohydrates, nucleic acids, lipids, polysaccharides, combinations thereof, synthetic inorganic molecules that cause a biological effect when administered in vivo to an animal and synthetic organic molecules that cause a biological effect when administered in vivo to an animal.

38. The method of claim 37, wherein the molecule is selected from the group consisting of substances detectable by x-ray, fluorescence, ultrasound, magnetic resonance imaging and radioactivity.

* * * * *